US006423887B1

(12) United States Patent
Rose-Fricker

(10) Patent No.: US 6,423,887 B1
(45) Date of Patent: Jul. 23, 2002

(54) GLYPHOSATE TOLERANT FESCUE GRASS VARIETY

(75) Inventor: Crystal Rose-Fricker, Canby, OR (US)

(73) Assignee: Pure Seed Testing, Inc., Canby, OR (US)

( * ) Notice: Subject to any disclaimer, the term of this patent is extended or adjusted under 35 U.S.C. 154(b) by 0 days.

(21) Appl. No.: 09/808,697

(22) Filed: Mar. 14, 2001

(51) Int. Cl.$^7$ .............................. A01H 5/00; A01H 5/10; A01H 1/04
(52) U.S. Cl. ..................... 800/320; 800/266; 800/300; 800/260
(58) Field of Search ................................ 800/320, 266, 800/300, 260; 47/58.1

(56) References Cited

FOREIGN PATENT DOCUMENTS

| WO | WO 92/04449 | 3/1992 |
| WO | WO 92/11764 | 7/1992 |

OTHER PUBLICATIONS

Rose–Fricker et al 1999, Registration of 'Tomahawk' tall fescue. Crop Science 39:288–289.*

Harrington et al., "Tolerance to Nerbicides of Ground Cover Species for New Zealand Orchards," *Plant Protection Quarterly* 13:111–116 (1998).

Comes et al., "Differential Response to Glyphosate and Growth Patterns of Red Fescue Fescue–Rubra." *J. Aquatic Plant Management* 23:32–35 (1985) Abstract.

Turf–Seed, Inc., Pure Seed Testing, Inc., *Field Day 14*, Jun. 20, 1996, Front cover and pp. 39–43 and 98–101.

Turf–Seed, Inc., Pure Seed Testing, Inc., *Field Day 15*, Jun. 27, 1997, Front cover and pp. 60–67.

Turf–Seed, Inc., Pure Seed Testing, Inc., *Field Day 16*, Jun. 18, 1998, Front cover and pp. 60–74.

Turf–Seed, Inc., Pure Seed Testing, Inc., *Field Day 17*, Jun. 15, 1999, Front cover and pp. 44–45.

\* cited by examiner

*Primary Examiner*—David T. Fox
*Assistant Examiner*—David H Kruse
(74) *Attorney, Agent, or Firm*—Klarquist Sparkman, LLP

(57) ABSTRACT

A glyphosate-tolerant tall fescue (*Festuca arundinacea*) variety in one form known as Tomahawk RT (experimental code PST-5MU), seed used to produce the grass, and methods of using the grass plant and the seed are provided. This grass is suitable for use in lawns, golf courses, sod, and other turfs where weeds are a problem. Weed control in areas planted with the disclosed grasses can be achieved by direct application of glyphosate herbicides.

38 Claims, 1 Drawing Sheet

GLYPHOSATE TOLERANT FESCUE GRASS VARIETY

FIELD

This disclosure relates to a tall fescue grass that is tolerant to glyphosate at levels sufficient to remove grass weed species from various turfs. One embodiment of this grass is known as Tomahawk RT (experimental code PST-5MU).

BACKGROUND

Fescue grasses (Festuca species) are widely used as turf in a variety of applications, including home lawns, golf courses, athletic fields, parks, pasture and along roadsides. Two types of fescue grasses are most commonly grown: tall fescues and fine fescues. Tall fescue grasses (such as *F. arundinacea*) have excellent drought and wear resistance. Tall fescue is adapted to a wide range of climactic conditions and is the most predominant cool-season, perennial grass in the United States. (See *Tall Fescue*, Edited by Buckner and Bush, Published by the American Society of Agronomy, Crop Science Society of America, and Soil Science Society of America. ASA Monograph Number 20. 1979. ISBN 0-89118-057-5). The term fine fescue encompasses several sub-types including hard fescue grasses (*F. longifolia*); these grasses are low maintenance and shade tolerant, but lack the durability of tall fescue grasses.

Glyphosate (N-(phosphonomethyl) glycine) is the active ingredient in glyphosate herbicides, such as ROUNDUP® brand herbicide produced by Monsanto, St. Louis, Mo. Typically, glyphosate is formulated as a water-soluble salt such as an ammonium, alkylamine, alkali metal or trimethylsulfonium salt. One of the most common formulations is the isopropylamine salt of glyphosate, which is the form employed in ROUNDUP® brand herbicide.

Glyphosate is a broad spectrum herbicide that inhibits the enzyme enolpyruvylshikimate-phosphate synthase (ESPS). It is conventionally applied as an aqueous solution to the foliage of plants, where it is taken up into the leaves and transported throughout the plant. Commercial formulations of glyphosate may also include one or more surfactants to facilitate penetration of the active ingredient into the plant leaves, as well as compounds to enhance rainfastness. Numerous U.S. patents disclose various formulations of glyphosate, including U.S. Pat. Nos. 4,405,531; 5,118,338; 5,196,044; 5,639,711; 5,652,197; 5,679,621; and 5,750,468.

Little success has been reported in finding natural resistance to glyphosate herbicides in plants. This is beneficial in one respect since it indicates that the likelihood of glyphosate resistant populations of weeds arising is low, but it also means that no naturally resistant desirable plant species are available. As a result, great care must be taken when applying glyphosate herbicides in the vicinity of desirable plants (e.g., crops, ornamentals, grass turf). Glyphosate herbicides are highly effective against grass species and therefore has not been previously known to be effectively applied to control weed growth in turf grasses.

SUMMARY OF THE DISCLOSURE

Herein disclosed is a tall fescue which is sufficiently glyphosate tolerate to survive applications of glyphosate herbicides at levels which are sufficient to kill many common grass weeds that grow in fescue plantings. One embodiment of such a glyphosate tolerate tall fescue is termed Tomahawk RT (Tomahawk ROUNDUP® Tolerant; experimental code PST-5MU). As used herein, a glyphosate-tolerant fescue grass is capable of tolerating application of herbicide effective applications, such as at least about ¼ pint per acre, such as at least about ½ pint per acre, of agricultural grade formulations of glyphosate-based herbicides (such as ROUNDUP®) brand herbicide produced by Monsanto, St. Louis, Mo.) (equivalent to application of approximately 0.014 g/square meter and 0.028 g/square meter of the active ingredient, glyphosate, respectively). In another embodiment, a glyphosate-tolerant fescue grass is capable of tolerating application of herbicide effective applications, such up to about 1 pint per acre, of agricultural grade formulations of glyphosate-based herbicides (such as ROUNDUP® brand herbicide produced by Monsanto, St. Louis, Mo.) (equivalent to application of approximately 0.056 g/square meter of the active ingredient, glyphosate) In one embodiment, Tomahawk RT is tolerant to application of least ¼ pint per acre of agricultural grade formulations of glyphosate-based herbicides (equivalent to application of approximately 0.014 g/square meter of glyphosate). In another embodiment, Tomahawk RT is tolerant to application of least ½ pint per acre of agricultural grade formulations of glyphosate-based herbicides (equivalent to application of approximately 0.028 g/square meter of glyphosate). In another embodiment, Tomahawk RT is tolerant to application of up to about 1 pint per acre of agricultural grade formulations of glyphosate-based herbicides (equivalent to application of approximately 0.056 g/square meter of glyphosate). Use of this grass as turf (for example in lawns, on golf courses, in parks, and along roadsides) permits ready control of weeds by application of a glyphosate herbicide. In addition, the Tomahawk RT variety has been observed under growing conditions in Hubbard, Oregon to have a mature plant height from about 120 cm to about 130 cm, a flag leaf height from about 58 cm to about 68 cm, a panicle length from about 19 cm to about 21 cm, and from about 55 to about 86 tillers per 12.7 cm of seeded row.

At least 2500 seeds of the Tomahawk RT variety have been deposited with the American Type Culture Collection (ATCC, Manassas, Va.; ATCC Deposit No.: PTA-2815). Therefore, these seeds are known and readily available to the public.

In one embodiment, the disclosure provides tall fescue plants having the morphological and physiological characteristics of Tomahawk RT, as well as seeds of such plants. In another embodiment, the disclosure provides tall fescue plants having the genotype of Tomahawk RT. The disclosure also encompasses tall fescue plants that are produced by crossing Tomahawk RT with other grass varieties, as well as seeds of such plants. In another aspect, the present disclosure provides a method of producing grass seed, comprising planting seed from Tomahawk RT under conditions that result in the germination of the seed, growth of grass plants and setting of progeny seed, and then harvesting the progeny seed.

The present disclosure also provides a method of producing a glyphosate-tolerant grass plant by crossing a first grass plant with one or more other grass plants to produce progeny grass plants, wherein the first grass plant is a Tomahawk RT variety or a glyphosate-tolerant cross derived from the Tomahawk RT variety, and then screening the progeny grass plants to select a progeny grass plant that is tolerant to glyphosate. Glyphosate-tolerant grass plants produced by this method are also encompassed by the disclosure.

These and other aspects of the present disclosure will become more apparent from the following description.

DETAILED DESCRIPTION OF SEVERAL EMBODIMENTS

EXAMPLE 1

Figure 1:
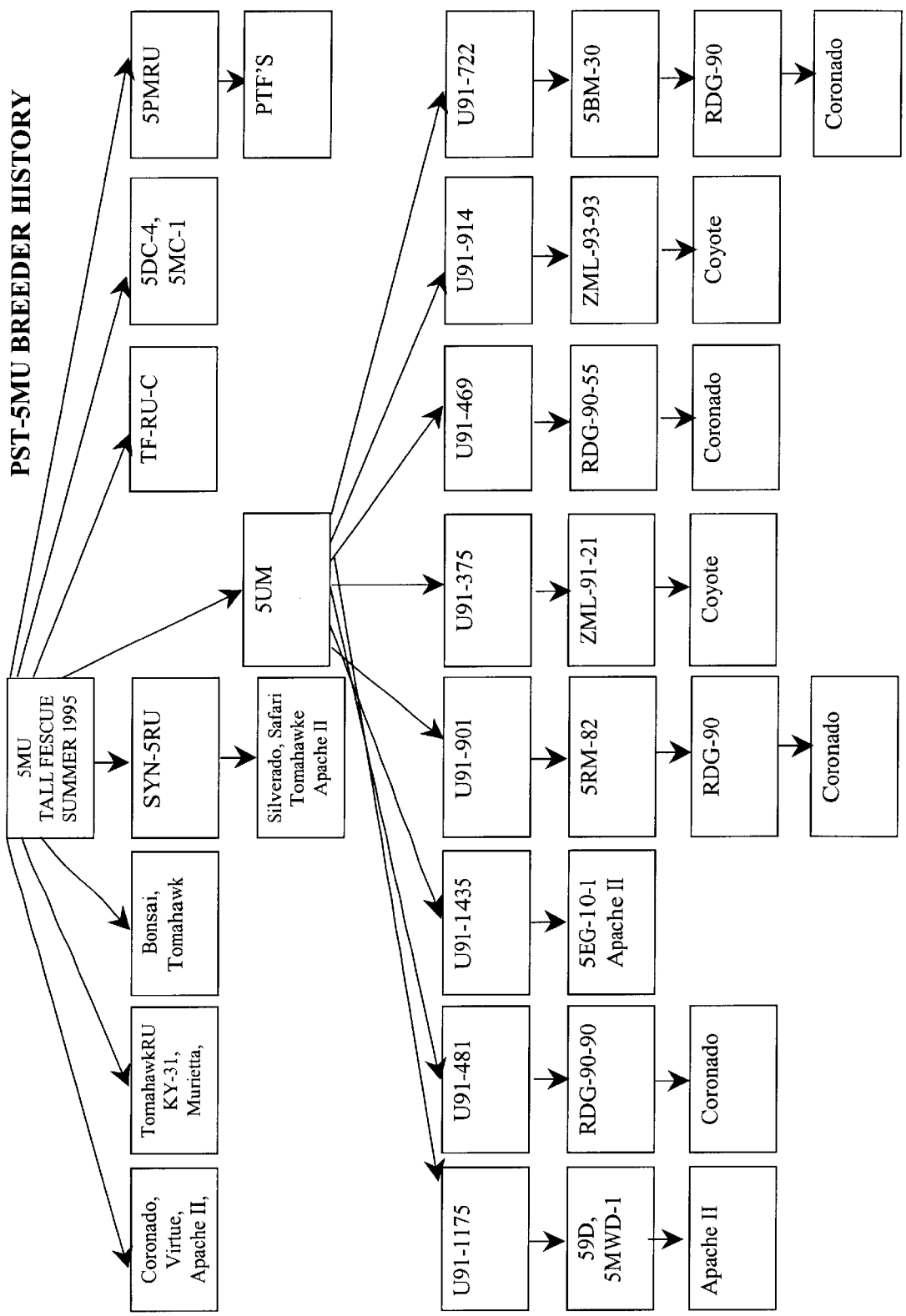
FIG. 1 is a flow chart showing the breeder history of PST-5MU.

Origin and Breeding History of Tall Fescue Variety Tomahawk RT (PST-5-MU)

The Tomahawk RT tall fescue (*Festuca arundinacea*) variety was developed by Pure Seed Testing, Inc. A summary of the Tomahawk RT breeder history is shown in FIG. 1. This variety was developed for its tolerance to glyphosate. The plants used in this project were screened by applying a selective pressure method which allowed for the selection of surviving plants treated with glyphosate at various stages of growth, as disclosed herein.

PST-5MU is an advanced generation synthetic cultivar selected from a breeding program involving the progenies of 22 parental clones. The parental clones were allowed to interpollinate in an isolated polycross nursery the summer of 1995. Sources of the polycross plants trace to the following sources: two from Virtue, two from Coronado, three from Apache II, four from Tomahawk, one from Kentucky 31, one from Bonsai, one from Murietta, two from 5RU, two from 5UM and one from Chesapeake. 5UM traces back to selections from Coronado, Apache II and Coyote. The remaining parental clones are the result of three separate screening trials.

The first screening trial began the fall of 1990 with seeded rows planted with a nybex planter. Stem rust resistant populations of Silverado and Safari, along with Tomahawk and Apache II were used. At six months of growth, an application of 1 quart per acre glyphosate (equivalent to application of approximately 0.112 g/square meter of glyphosate) was performed in March of 1991. The best 23 survivors with good color and growth were selected and moved into an isolated polycross nursery prior to pollination and called 5RU. This was approximately less than 1% of the total population screened. Progenies from these 23 clones were used in further screening trials the summer of 1993. In a greenhouse seedlings were sprayed with glyphosate at the three to four leaf stage at one quart per acre. Seventy-four out of 150 (50%) survived and were transplanted to the field in June 1994. Two of the survivors were selected as parental clones of PST-5MU in the spring of 1995.

In the fall of 1991, another screening nursery was established with seeded rows of five Pure Seed Testing cultivars and experimental populations near Hubbard, Oregon. During the spring of 1992, glyphosate was applied at various rates in a circular pattern across the rows ranging from $1/8^{th}$ of a pint to 2 quarts per acre. Survivors from Coronado, Apache II and Tomahawk were vegetatively cloned early September 1992 and sprayed with 1 quart per acre glyphosate with WA-100 in cell pack planting flats 1 month later. The survivors (5%) were transplanted into an isolated polycross nursery in December of 1992. During the summer of 1993, seed was harvested from each cloned row of this nursery after being rouged for uniformity and stem rust resistance and allowed to interpollinate. Seedlings were started from each clonal row and screened in the greenhouse the winter of 1993 with 1 quart per acre of glyphosate.

At the same time seedlings from seventeen commercially available varieties and one PST experimental population were also sprayed in the greenhouse for the third screening trial. All survivors, approximately 1 to 10% of each variety and 10 to 25% of previously screened progenies, were transplanted to an isolated nursery in June of 1994. From this nursery the 22 parents of PST-5MU were selected for good seed head number, stem rust resistance and an overall attractive appearance with dark green color. Seed of each parental clone of PST-5MU was used in the fall of 1995 for progeny testing in turf trials in Oregon and North Carolina. The turf trial in Oregon was sprayed in April of 1996 with ½ pint per acre glyphosate (equivalent to application of approximately 0.028 g/square meter of glyphosate).

In the fall of 1996, progenies of the best eight parental clones for turf quality and surviving one pint per acre of glyphosate with little yellowing in turf trials were sprigged to start a breeder seed nursery. This nursery comprised 1170 plants which trace back maternally to Apache II, Safari, Virtue, Bonsai, Tomahawk and Silverado. In this nursery approximately half of the plants trace to the Tomahawk parentage. This nursery was sprayed in the spring of 1997 with one quart glyphosate per acre. Survivors were harvested and seed was used to establish a space plant nursery fall 1997 of 3,650 plants. This nursery was sprayed with one pint of glyphosate per acre in March of 1998. The best nine percent (331 plants) with no glyphosate damage were allowed to interpollinate and harvested in the summer of 1998. This nursery was sprayed again in the spring of 1999 with one pint per acre glyphosate. The nursery was rogued for uniformity, dark green color, overall disease resistance and the plants with no discoloration or stunting from glyphosate. Two hundred plants were harvested as the breeder seed of Tomahawk RT (experimental code PST-5MU).

Seed propagation is limited to three generations of increase from breeder seed: one each of foundation, registered and certified. Breeder seed is maintained at Pure Seed Testing, Inc., in Oregon. Tomahawk RT is a stable and uniform variety. No off-types or variants have been observed in the reproduction or multiplication of this variety from the breeder seed nursery to the foundation field.

EXAMPLE 2

Seed Deposits

Seeds of the tall fescue variety Tomahawk RT (experimental code PST-5MU) were deposited with the ATCC (Manassas, Va.) on Dec. 18, 2000 under accession number PTA-2815. The variety is also maintained at, and available from, Pure Seed Testing, Inc., P.O. Box 449, Hubbard, Oreg. 97032.

EXAMPLE 3

Description of Plants

The following growth characteristics were observed for Tomahawk RT plants that were approximately one or two years old, grown in seeded rows near Hubbard, Oreg. Variations on these measurements may be observed for plants of differing ages, grown in other locations and/or under different prevailing weather conditions.

TABLE 1

Growth Characteristics of the Tomahawk RT Variety*

| Characteristic | Mean[a] | Mean[b] | Mean[c] |
|---|---|---|---|
| Plant Height | 126.4 | 122.2 | 130.9 |
| Flag Leaf Height | 68.2 | 58.5 | 66.5 |
| Internode Length | 27.8 | 24.3 | 26.1 |
| Tiller Leaf Length | 17.9 | 19.1 | 18.6 |
| Tiller Leaf Width (mm) | 5.1 | 4.5 | 4.4 |
| Flag Leaf Length | 12.7 | 12.7 | 13.9 |

TABLE 1-continued

Growth Characteristics of the Tomahawk RT Variety*

| Characteristic | Mean[a] | Mean[b] | Mean[c] |
|---|---|---|---|
| Flag Leaf Width (mm) | 4.6 | 3.8 | 4.6 |
| Panicle Length | 18.9 | 20.6 | 21.1 |
| Tiller Count (per 12.7 cm of seeded row) | 55.9 | 55.0 | 85.6 |

*All length measurements are in cm unless otherwise indicated. Mean morphological measurements taken on a tall fescue seed yield trial in 1999[a] and 2000[b,c] seeded in the fall of 1998[a,b] or 1999[c] near Hubbard, Oregon.

Additionally, the information provided below relating to turf quality ratings (seasonal density, genetic color, and leaf texture) and disease resistance (leaf spot) is derived from various turf trials. These data are expressed in numbers ranging from 1–9, with 1 representing low turf quality or low disease resistance and 9 representing desirable high turf quality and no disease.

The Tomahawk RT variety is additionally characterized by the following results from various trials.

The mean turf quality ratings for the Tomahawk RT variety in a tall fescue turf trial that was seeded in the fall of 1995 near Hubbard, Oreg. were 5.1 in 1996, 5.5 in 1997, 6.0 in 1998, and 6.1 in 1999 (9=best).

The mean summer turf quality ratings for the Tomahawk RT variety in a tall fescue turf trial that was seeded in the fall of 1995 near Rolesville, N.C. were 4.7 in 1996 and 6.5 in 1997 (9=best).

The mean brown patch rating for the Tomahawk RT variety in a tall fescue turf trial that was seeded in the fall of 1995 near Rolesville, N.C. was 4.5 in 1996 and 5.7 in 1997 (9=no disease).

The mean spring green-up, winter color, and turf quality ratings for the Tomahawk RT variety in a tall fescue turf trial that was seeded in the fall of 1998 near Hubbard, Oreg. were 4.3, 4.7, and 5.8, respectively in 1999 (9=completely green; dark green; ideal quality, respectively).

The susceptibility of tall fescue to gray leaf spot (*Pyricularia grisea*) was measured as follows. A tall fescue turf evaluation trial was seeded 1 Sep at a rate of 6 lb/1000 ft$^2$ near Rolesville, N.C. The trial consisted of commercially available cultivars and advanced experimental synthetic varieties seeded into 3'×5' plots. Each entry was replicated twice in a randomized complete block design. The plots received 2 lb N/1000 ft$^2$ during the first six weeks of establishment and were mowed three times per week at a two-inch height. Four weeks after seeding, symptoms of a leaf spot disease (which occurred naturally) were visible. Initial symptoms were tan lesions with dark borders. Symptom severity increased during the next two weeks, resulting in "melting-out" of highly susceptible cultivars and experimental varieties. Microscopic examination of infected leaves yielded the presence of *Pyricularia grisea* conidia. Significant difference in gray leaf spot susceptibility existed among tall fescue entries, with the Tomahawk RT variety having a mean disease rating of 8.0 and Tomahawk having a disease rating of 4.5 (9=no visible symptoms; rating is the mean of two replicates).

EXAMPLE 4

Glyphosate Tolerance Characteristics

The following tables show examples of field trials in which the glyphosate resistance characteristics of the Tomahawk RT variety were examined and compared to currently used tall fescue grass varieties. Grasses were seeded in the fall of 1998 near Hubbard, Oreg. and rated between November 1998 and September 1999.

Table 2 shows comparisons of the turf quality of the Tomahawk RT variety with other tall fescue varieties in the absence of glyphosate herbicide (as an unsprayed check). The score ratings are based on a scale of 1 to 9, typical of rating scales for turf grasses (9=ideal quality; no disease).

TABLE 2

Tall Fescues in the Absence of Glyphosate.

| | Turf quality (no herbicide) | | | | Summer Stress |
|---|---|---|---|---|---|
| Variety | 26 Jan | 1 April | 1 May | 1 June | 24 Sept |
| Tar Heel | 5.3 | 6.0 | 6.0 | 5.3 | 8.0 |
| Wolfpack | 6.3 | 7.3 | 6.5 | 5.5 | 7.3 |
| Tomahawk RT | 5.5 | 6.8 | 6.3 | 6.3 | 6.5 |
| Pure Gold | 4.8 | 5.5 | 5.8 | 6.3 | 6.5 |
| Tomahawk E | 5.8 | 6.0 | 5.5 | 5.8 | 5.8 |
| 5HU | 5.0 | 6.0 | 6.5 | 5.8 | 5.0 |
| Kentucky 31 | 3.8 | 3.5 | 3.0 | 3.0 | 4.3 |
| LSD (0.05)* | 1.3 | .09 | 1.3 | 1.4 | 1.8 |

*To determine statistical differences among entries, subtract one entry's mean from another entry's mean. Statistical differences occur when this value is equal to or larger than the corresponding L.S.D. value.

Table 3 shows comparisons of the turf quality of the Tomahawk RT variety with other tall fescue varieties in the absence of glyphosate herbicide and the damage to the grasses produced by application of a commercial formulation of glyphosate sprayed at the rate of ½ pint (8 oz.) per acre on Mar. 2, 1999. The score ratings are based on a scale of 1 to 9. For herbicide damage: 9 =no glyphosate damage; 8–7=10–20% yellowing; 6–5=30–40% yellowing with minor growth retardation; 4–3=50–60% yellowing with growth retardation; 2–1=70–90% yellowing with dead turf. For turf quality: 9=best turf quality, 0=dead turf. These results show that the Tomahawk RT variety was significantly more tolerant of glyphosate herbicide than currently available tall fescue varieties, while having at least as good turf quality.

TABLE 3

Tall Fescues in the Presence of 1/2 pint (8 oz.) per acre Glyphosate.

| | Turf quality (no herbicide) | | Summer Stress | Herbicide damage | |
|---|---|---|---|---|---|
| Variety | 26 Jan | 1 May | 24 Sept | 1 April | 20 April |
| Tomahawk RT | 6.8 | 6.8 | 6.5 | 7.5 | 7.3 |
| Pure Gold | 5.0 | 5.5 | 5.3 | 5.3 | 5.5 |
| Tar Heel | 5.3 | 5.5 | 7.0 | 5.0 | 5.0 |
| 5HU | 5.3 | 4.5 | 6.3 | 5.3 | 4.5 |
| Kentucky 31 | 4.0 | 3.3 | 4.5 | 3.3 | 3.8 |
| Tomahawk E | 6.5 | 4.5 | 6.3 | 4.3 | 3.8 |
| Wolfpack | 6.3 | 3.3 | 5.5 | 4.0 | 2.8 |
| LSD (0.05)* | 0.9 | 1.0 | 1.9 | 0.9 | 1.0 |

*To determine statistical differences among entries, subtract one entry's mean from another entry's mean. Statistical differences occur when this value is equal to or larger than the corresponding L.S.D. value.

Table 4 shows the effect of applying glyphosate herbicide at a levels of 1 pint (16 oz.) per acre to tall fescue grasses. Grasses were sprayed with 1 pint per acre glyphosate on Nov. 19, 1998 and ½ pint (8 oz.) per acre on Mar. 2, 1999. The effect of the herbicide application on turf quality and on glyphosate damage is shown, using a scale of 1 to 9 as described for Table 3 (9: ideal quality; no disease; no glyphosate damage). In addition, the percent of damage due to herbicide application (which indicates yellowing, stunting, and death) is shown.

TABLE 4

Tall Fescues in the Presence of 1 pint per acre Glyphosate

| Variety | Turf quality (no herbicide)* | | | | Summer Stress* | Herbicide damage | | | |
|---|---|---|---|---|---|---|---|---|---|
| | 26 Jan | 1 Apr | 20 Apr | 1 May | 24 Sept | % 26 Dec | * 26 Jan | * 2 Mar | % 1 Apr |
| Tomahawk RT | 4.3 | 6.3 | 6.0 | 6.5 | 7.8 | 21.3 | 5.3 | 5.3 | 72.5 |
| Wolfpack | 3.5 | 3.3 | 4.5 | 4.8 | 7.8 | 52.5 | 3.3 | 3.3 | 41.3 |
| Pure Gold | 3.5 | 3.8 | 3.8 | 4.8 | 7.3 | 33.8 | 4.0 | 3.3 | 41.3 |
| Tar Heel | 2.0 | 3.0 | 4.0 | 5.0 | 7.5 | 76.3 | 2.3 | 3.3 | 40.0 |
| Tomahawk E | 2.8 | 2.8 | 3.5 | 4.5 | 7.3 | 65.0 | 2.5 | 2.3 | 36.3 |
| 5HU | 3.3 | 2.8 | 3.8 | 4.8 | 7.0 | 45.0 | 3.8 | 3.5 | 33.8 |
| Kentucky 31 | 2.0 | 2.0 | 3.3 | 4.0 | 5.8 | 75.0 | 2.0 | 2.8 | 33.8 |
| LSD (0.05) | 0.8 | 1.7 | 1.6 | 1.3 | 0.9 | 11.8 | 1.1 | 1.1 | 14.9 |

*Ranked on a scale of 1–9; % damage.

The data above demonstrate that Tomahawk RT plants are tolerant to glyphosate herbicide applied at levels and/or frequency sufficient to remove weed species from lawns, pasture, golf courses, etc. As used herein the phrase "a glyphosate tolerant grass plant" is a grass plant that will survive application of agricultural formulations of glyphosate herbicide (containing 41% w/v glyphosate) at levels equivalent to up to 1 pint per acre, corresponding to at least about 0.056 g per square meter of active ingredient glyphosate. This level of glyphosate is sufficient to kill some common grass weeds.

At the application rate of ½ pint per acre of glyphosate herbicide (containing 41% w/v glyphosate) and under the field conditions prevailing at the time the field tests were performed on Tomahawk RT (January through September 1999 near Hubbard, Oreg.), only minor amounts of yellowing of the grass was observed, and no substantial reduction in growth rate was detected (Table 3). However, more significant deleterious effects may be observed depending on the age of the grass, the time of year and the prevailing weather conditions. For example, it has been observed that the Tomahawk RT variety is more sensitive to glyphosate herbicide (containing 41% w/v glyphosate) applications if the ambient temperature of the plants decreases below about 32° C. or exceeds about 90° C. In addition, the Tomahawk RT variety is more sensitive to glyphosate if the glyphosate herbicide (containing 41% w/v glyphosate) is applied during the seedling stage, for example within the first 60-days of planting. Tomahawk RT may tolerate additional applications of ½ pint per acre of glyphosate herbicide the following spring or fall after seeding, where necessary to remove weeds that are difficult to control. However, when re-applying glyphosate herbicide, the sensitivity of the Tomahawk RT variety to ambient temperature, time of year, and age of the grass should be considered.

Higher levels of glyphosate herbicide can be applied to Tomahawk RT plants if necessary to eradicate particularly recalcitrant weed species. As shown in Table 4, Tomahawk RT can tolerate application of up to 1 pint per acre of agricultural formulations of glyphosate herbicide (equivalent to about 0.056 g per square meter of active ingredient glyphosate) depending on the time of year, age of the plants and environmental conditions. At this level of glyphosate application, more yellowing of the grasses and a substantial retardation of plant growth can be observed, but the grass plants not killed subsequently make a complete recovery.

EXAMPLE 5

Production of Glyphosate-Tolerant Grasses

Tomahawk RT can be grown under normal conditions for growing turf grasses, and bulk seed for large-scale planting can be obtained by methods known in certified seed production. For example, bulk seed may be produced by planting Tomahawk RT variety seeds obtained from either ATCC (PSA-2815) or Pure Seed Testing, Inc., allowing the mature plants to produce seed by cross-pollination with each other and then collecting the seed. Standard precautions should be taken to prevent cross-pollination from other grasses, such as growing the variety in an isolated plot of sterilized soil, removing adjacent vegetation, etc. The Tomahawk RT variety seeds deposited with ATCC are breeder seeds; propagation of plants from these seeds can be performed under the conditions specified in the 1998 Oregon Certified Seed Handbook, published by Oregon State University Extension Service, Corvallis, Oreg. 97331.

The Tomahawk RT variety can also be asexually reproduced via vegetative propagules, such as sprigs, plugs, and sod.

To confirm maintenance of the glyphosate-tolerance characteristic, a glyphosate herbicide (containing 41% w/v active ingredient glyphosate) can be applied to the plants at the equivalent of at least ¼ pint per acre, for example at least ½ pint per acre, for example up to 1 pint per acre.

EXAMPLE 6

Exemplary Uses of the Glyphosate Tolerant Grass Tomahawk RT

The tall fescue variety Tomahawk RT can be used in the same way as other tall fescue varieties. However, the resistance to glyphosate herbicides affords the Tomahawk RT variety particular advantages over other varieties. For example, with current commercially available varieties of fescue grasses, the preparation of a lawn that is to be made by seeding requires extensive preparation of the soil to remove weeds that may be present, often including soil fumigation. With Tomahawk RT, such preparation can be avoided since some weeds that begin to grow in the new lawn are readily removed by application of a glyphosate herbicide. With Tomahawk RT, glyphosate herbicides can also be used to remove many of the most troublesome lawn weeds such as crabgrass (*Digitaria sanguinalis*), annual bluegrass (*Poa annua*), rattail fescue (*Vulpia myuros*) and annual ryegrass (*Lolium multiforum*). Thus, the Tomahawk RT variety is especially marketable and therefore useful.

EXAMPLE 7

Introducing Traits of the Tomahawk RT Variety Into Other Grass Varieties

The morphological and physiological characteristics of the Tomahawk RT variety of tall fescue, including the glyphosate tolerance trait, can be introduced into other grass varieties by conventional breeding techniques. For example, the Tomahawk RT variety can be grown in pollination proximity to another variety of tall fescue grass, allowing cross-pollination to occur between the Tomahawk RT variety and the other variety, and then harvesting the hybrid seeds. Plants grown from these hybrid seeds can then be tested for the maintenance of the molecular characteristics described above for the Tomahawk RT variety, and/or the plants can simply be observed to see if they display the same growth characteristics described in the above tables.

For example, plants grown from these hybrid seeds can be tested for glyphosate tolerance by application of glyphosate herbicide at various levels. In this way, the glyphosate tolerance characteristic may be combined with other desirable plant characteristics. Thus, the provision of Tomahawk RT enables the production of progeny plants of Tomahawk RT having the glyphosate tolerance characteristic. "Progeny plants" of Tomahawk RT are any plants that are the offspring of a cross between Tomahawk RT and any other plant or plants. Progeny plants also include successive generations of the offspring, for example those selected for glyphosate tolerance using the methods described herein. First-generation progeny plants may retain the glyphosate tolerance characteristic of the Tomahawk RT parent. However, if a first-generation progeny plant does not retain the desired level of glyphosate tolerance observed with Tomahawk RT, subsequent generations of offspring can be recycled for glyphosate tolerance which have at least the same resistance characteristics of Tomahawk RT described herein, such capable of tolerating application of at least about ¼ pint per acre, such as at least about ½ pint per acre, for example up to 1 pint per acre of a glyphosate herbicide (containing 41% w/v active ingredient glyphosate). In one embodiment, subsequent generations of offspring can have a glyphosate tolerance that exceeds that of Tomahawk RT, for example capable of tolerating application of at least 1 pint per acre, for example at least 1 quart of a glyphosate herbicide (containing 41% w/v active ingredient glyphosate).

In addition, Tomahawk RT can be used as transformation targets for the production of transgenic grasses. In certain embodiments, the present disclosure contemplates the transformation of cells derived from the Tomahawk RT variety with at least one transgene. For example, transgenes that can be used, include, but are not limited to, transgenes that confer resistance to herbicides, insect, disease (viral. bacterial, fungal, nematode) or drought resistance, standability, prolificacy, salt damage resistance, and quality are useful. Examples of such genes and methods of transforming plants are described in U.S. Pat. No. 6,025,545 to Lundquist et al., herein incorporated by reference.

Having illustrated and described the principles of the disclosure in multiple embodiments and examples, it should be apparent to those skilled in the art that the disclosure can be modified in arrangement and detail without departing from such principles. The invention, therefore, encompasses all modifications coming within the spirit and scope of the following claims.

What is claimed is:

1. A tall fescue grass plant, having all of the morphological and physiological properties of a grass plant grown from the seed deposited under American Type Culture Collection (ATCC) No: PTA-2815.

2. The grass plant of claim 1, wherein the grass plant is in a sod.

3. The grass plant of claim 1, wherein the grass plant is in a golf course fairway.

4. The grass plant of claim 1, wherein the grass plant is in a golf course rough.

5. The grass plant of claim 1, wherein the grass plant is in a lawn.

6. The grass plant of claim 1, wherein the grass plant is in an athletic field.

7. The grass plant of claim 1, wherein the grass plant is in a park.

8. Progeny of a grass plant according to claim 1.

9. Seed of the grass plant of claim 1.

10. A seed mixture, comprising the seed of claim 9.

11. A method of producing grass seed, comprising (a) planting grass seed according to claim 9 under conditions that result in the germination of the seed, growth of grass plants and setting of progeny seed; and (b) harvesting the progeny seed.

12. Grass seed produced by the method of claim 11.

13. A mixture of grass seed comprising the grass seed of claim 12.

14. A vegetative sprig or clone of the grass plant of claim 1.

15. The grass plant of claim 1, further comprising at least one transgene.

16. Seed resulting from crossing the grass plant of claim 1 with a second grass plant.

17. The seed of claim 13, wherein the second grass plant is a tall fescue grass plant.

18. A grass plant grown from the seed of claim 16.

19. The grass plant of claim 18, wherein the grass plant is in a sod.

20. The grass plant of claim 18, wherein the grass plant is in a golf course fairway.

21. The grass plant of claim 18, wherein the grass plant is in a golf course rough.

22. The grass plant of claim 18, wherein the grass plant is in a lawn.

23. The grass plant of claim 18, wherein the grass plant is in an athletic field.

24. The grass plant of claim 18, wherein the grass plant is in a park.

25. A method of producing a glyphosate-tolerant grass plant, comprising:

(a) crossing a first grass plant with at least one other grass plant to produce progeny grass plants, wherein the first grass plant is the grass plant of claim 1;

(b) screening the progeny grass plants to select a progeny grass plant that is tolerant to glyphosate.

26. A glyphosate-tolerant grass plant produced by the method of claim 25.

27. The glyphosate-tolerant grass plant of claim 26, wherein the grass plant is in a sod.

28. The glyphosate-tolerant grass plant of claim 26, wherein the grass plant is in a park.

29. The glyphosate-tolerant grass plant of claim 26, wherein the grass plant is in a golf course rough.

30. The glyphosate-tolerant grass plant of claim 26, wherein the grass plant is in a lawn.

31. The glyphosate-tolerant grass plant of claim 26, wherein the grass plant is in an athletic field.

32. The glyphosate-tolerant grass plant of claim 26, wherein the grass plant is in a park.

33. A vegetative s prig or clone of the glyphosate-tolerant grass plant of claim 26.

34. The glyphosate-tolerant grass plant of claim 26, further comprising at least one transgene.

35. A glyphosate-tolerant grass plant according to claim 26 wherein the grass plant is tolerant to application of up to about 0.056 g per square meter of glyphosate.

36. A glyphosate-tolerant grass plant according to claim 26 wherein the grass plant is tolerant to application of at least about 0.028 g per square meter of glyphosate.

37. A glyphosate-tolerant grass plant according to claim 26 wherein the grass plant is tolerant to application of at least about 0.014 g per square meter of glyphosate.

38. Grass seed deposited as ATCC No: PTA-2815.

* * * * *

UNITED STATES PATENT AND TRADEMARK OFFICE
CERTIFICATE OF CORRECTION

PATENT NO.   : 6,423,887 B1
DATED        : July 23, 2002
INVENTOR(S)  : Crystal Rose-Fricker It is certified that error appears in the above-identified patent and that said Letters Patent is hereby corrected as shown below:

<u>Column 9,</u>
Line 46, the period "." after "viral" should be a comma -- , --.

<u>Column 10,</u>
Line 28, "The seed of claim 13" should be -- The seed of claim 16 --.
Line 64, "s prig" should be -- sprig --.

Signed and Sealed this

Twenty-fourth Day of December, 2002

JAMES E. ROGAN
*Director of the United States Patent and Trademark Office*